United States Patent [19]

Tsai

[11] Patent Number: 5,206,205
[45] Date of Patent: Apr. 27, 1993

[54] THERMAL TREATMENT OF SUPERABSORBENTS TO ENHANCE THEIR RATE OF ABSORBENCY UNDER LOAD

[75] Inventor: Chuan-Ling Tsai, Appleton, Wis.

[73] Assignee: Kimberly-Clark Corporation, Neenah, Wis.

[21] Appl. No.: 800,877

[22] Filed: Nov. 27, 1991

Related U.S. Application Data

[63] Continuation-in-part of Ser. No. 745,319, Aug. 15, 1991, abandoned.

[51] Int. Cl.$^5$ .................................................. B01J 20/26
[52] U.S. Cl. ................................. 502/402; 502/401; 502/404; 604/368
[58] Field of Search .............. 502/401, 402, 404; 604/368

[56] References Cited

U.S. PATENT DOCUMENTS

| | | | |
|---|---|---|---|
| 2,486,805 | 11/1949 | Seymour et al. | 117/68 |
| 2,639,239 | 5/1953 | Elliott | 106/197 |
| 2,772,999 | 12/1956 | Masci et al. | 167/84 |
| 2,773,000 | 12/1956 | Masci et al. | 167/84 |
| 3,379,720 | 4/1968 | Reid | 260/232 |
| 3,723,413 | 3/1973 | Chatterjee et al. | 260/232 |
| 3,731,686 | 5/1973 | Chatterjee | 128/285 |
| 3,858,585 | 1/1975 | Chatterjee | 128/290 |
| 4,044,766 | 8/1977 | Kaczmarzyk et al. | 128/285 |
| 4,127,944 | 12/1978 | Giacobello | 34/9 |
| 4,200,736 | 4/1980 | Shinohara et al. | 536/87 |
| 5,005,771 | 4/1991 | Pieh et al. | 241/23 |

FOREIGN PATENT DOCUMENTS

WO91/02552  3/1991  PCT Int'l Appl. .

Primary Examiner—Patrick P. Garvin
Attorney, Agent, or Firm—Gregory E. Croft

[57] ABSTRACT

The absorbent capacity of superabsorbent materials, as measured under an applied load, is significantly increased by treating the superabsorbent material at a temperature of about 125° C. or greater for a sufficient period of time.

20 Claims, 1 Drawing Sheet

THERMAL TREATMENT OF SUPERABSORBENTS TO ENHANCE THEIR RATE OF ABSORBENCY UNDER LOAD

This is a continuation-in-part of copending application Ser. No. 07/745,319, filed on Aug. 15, 1991, now abandoned.

BACKGROUND OF THE INVENTION

Superabsorbent materials are well known materials which have particular utility in absorbent personal products such as disposable diapers, training pants, incontinence garments, feminine pads and the like. As their name suggests, the purpose of superabsorbents is to absorb large quantities of liquid in amounts many times the weight of the superabsorbent material. One difficulty with many superabsorbent materials, however, is that the in-use absorbent capacity is less than that measured in the laboratory due to pressure or loading experienced under actual in-use conditions. In the case of a disposable diaper, for example, when the baby is sitting down, the weight of the baby causes increased pressure to be exerted on the superabsorbent, thereby decreasing its ability to absorb and hold liquid. To this end, there is continual effort to provide superabsorbent materials which have increased absorbent capacity in use.

SUMMARY OF THE INVENTION

It has now been discovered that the in-use absorbent capacity of superabsorbent materials, when measured under a load, can be improved by simply heating the superabsorbent material for a period of time at a sufficiently high temperature. This property of the superabsorbent material is measured by the Absorbency Under Load (AUL) test, which will be hereinafter described with reference to the drawing. Interestingly, the heat treatment of this invention has shown no positive effect on the free swell absorbent capacity of superabsorbent materials as normally measured without an applied load when using the same saline solution used to determine the AUL. The temperature/time relationship of the heat treatment of this invention must be optimized for each particular superabsorbent material, but in general, higher temperatures and longer times improve the AUL. Hence high temperature for a short treatment time can produce good results as well as low temperature for a long treatment time. In carrying out the method of this invention, the 2-minute AUL of the superabsorbent material is preferably increased about 1 gram per gram or greater.

Treatment temperatures from about 140° C. to about 210° C. have been shown to work well, although lower and higher temperatures can be used. A temperature of about 125° C. is considered to be the lower limit for practical purposes due to the correspondingly long time normally necessary to obtain sufficiently improved results. On the other hand, the upper treatment temperature is limited only by the ability of the superabsorbent material to withstand the temperature treatment without degrading or melting. For polyacrylate superabsorbent materials, for example, an upper temperature limit is about 350° C. For commercial purposes, the highest possible temperatures are preferred because of the attendant short treatment times. It is not necessary that the treatment temperature be held constant during the treatment. Accordingly the temperature can increase, decrease, or cycle up and down within the selected range.

The treatment time is preferably as short as possible, provided the 2 minute AUL of the superabsorbent material is increased at least about 1 gram per gram. When using an oven, however, treatment times are necessarily about 1 or 2 minutes or longer due to heat transfer limitations. Treatment times of from about 5 minutes to about 60 minutes have been used successfully, with a treatment time of about 20 minutes or less being preferred, more preferably about 10 minutes or less, and most preferably about 5 minutes or less. As stated above, the treatment time will be dependent on the temperature of the treatment.

Suitable superabsorbent materials include any substantially water-insoluble material which is capable of absorbing or gelling at least 10 times its weight, preferably 15 times its weight, of body exudate or a suitable aqueous solution such as a 0.9 weight percent solution of sodium chloride in distilled water. Such materials can include, but are not limited to, synthetic materials and modified natural materials and the like. Preferably the superabsorbent materials are once dried, as commercially received from the superabsorbent manufacturer (about 2 to about 7 weight percent moisture or less), prior to being subjected to the heat treatment of this invention. However, the heat treatment of this invention can also be applied during the initial drying of the superabsorbent material after it is made. By way of example, superabsorbent materials include, but are not limited to, hydrogel-forming polymers which are alkali metal salts of: poly(acrylic acid); poly(methacrylic acid); copolymers of acrylic and methacrylic acid with acrylamide, vinyl alcohol, acrylic esters, vinyl pyrrolidone, vinyl sulfonic acids, vinyl acetate, vinyl morpholinone and vinyl ethers; hydrolyzed acrylonitrile grafted starch; acrylic acid grafted starch; maleic anhydride copolymers with ethylene, isobutylene, styrene, and vinyl ethers; polysaccharides such as carboxymethyl starch, carboxymethyl cellulose, methyl cellulose, and hydroxypropyl cellulose; poly(acrylamides); poly(vinyl pyrrolidone); poly(vinyl morpholinone); poly(vinyl pyridine); and copolymers and mixtures of any of the above, and the like. The hydrogel-forming polymers are preferably lightly crosslinked to render them substantially water-insoluble. A preferable superabsorbent material is a lightly crosslinked poly(sodium acrylate). Crosslinking may be achieved by irradiation or by covalent, ionic, van der Waals attractions, or hydrogen bonding interactions, for example. The superabsorbent materials can be in any form suitable for use in absorbent structures, including particles, fibers, bicomponent fibers, filaments, flakes, spheres, and the like.

DETAILED DESCRIPTION OF THE DRAWING

Figure 1:
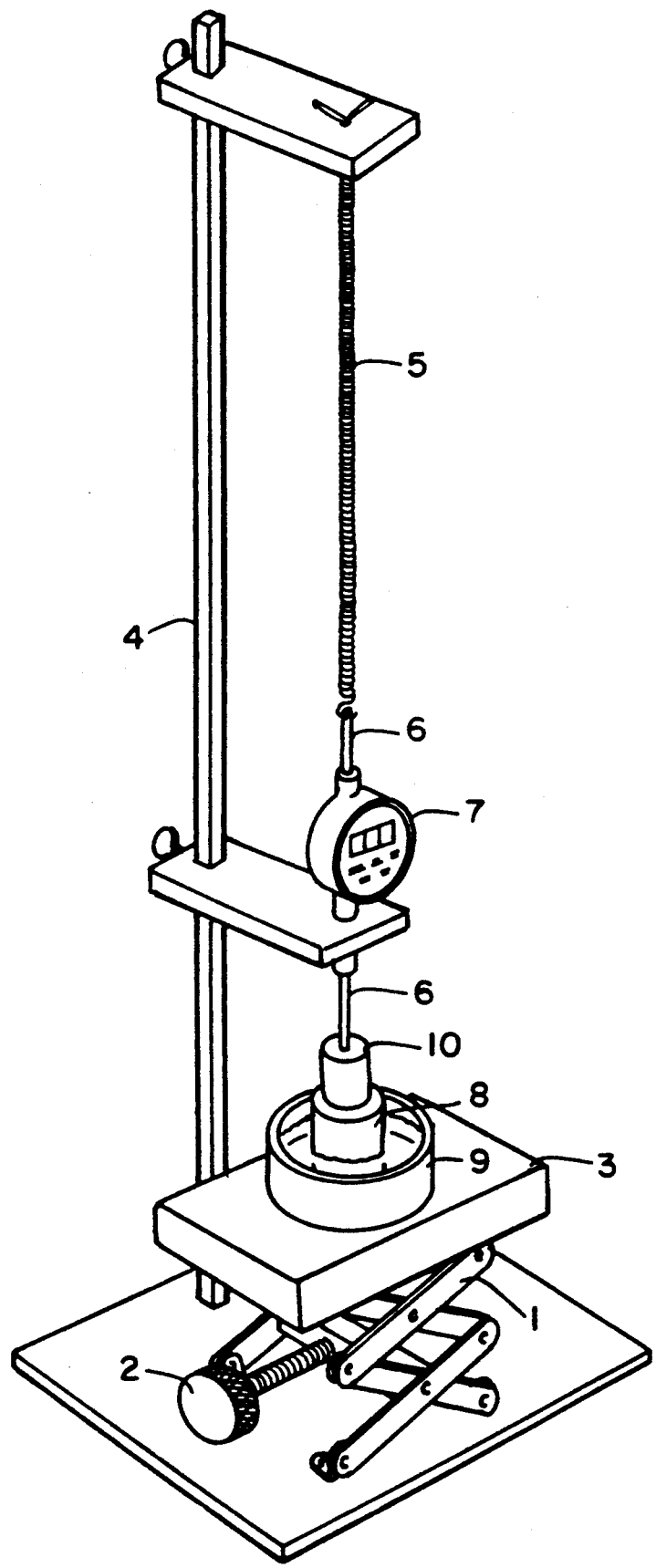
FIG. 1, the sole Figure in the drawing, is a schematic illustration of the apparatus used for measuring the Absorbency Under Load of a superabsorbent material.

The Absorbency Under Load (AUL) is a test which measures the ability of a superabsorbent material to absorb a liquid (0.9 weight percent solution of sodium chloride in distilled water) while under an applied load or restraining force.

Referring to FIG. 1, the apparatus and method for determining AUL will be described. Shown is a perspective view of the apparatus in position during a test. Shown is a laboratory jack 1 having an adjustable knob 2 for raising and lowering the platform 3. A laboratory stand 4 supports a spring 5 connected to a modified thickness meter probe 6, which passes through the housing 7 of the meter, which is rigidly supported by the laboratory stand. A plastic sample cup 8, which contains the superabsorbent material sample to be tested, has a liquid-permeable bottom and rests within a Petri dish 9, which contains the saline solution to be absorbed. A weight 10 rests on top of a spacer disc (not visible) resting on top of the superabsorbent material sample (not visible).

The sample cup consists of a plastic cylinder having a 1 inch inside diameter and an outside diameter of 1.25 inch. The bottom of the sample cup is formed by adhering a to the end of the cylinder by heating the screen above the melting point of the plastic and pressing the plastic cylinder against the hot screen to melt the plastic and bond the screen to the plastic cylinder.

The modified thickness meter used to measure the expansion of the sample while absorbing the saline solution is a Mitutoyo Digimatic Indicator, IDC Series 543, Model 543-180, having a range of 0-0.5 inch and an accuracy of 0.00005 inch (Mitutoyo Corporation, 31-19, Shiba 5-chome, Minato-ku, Tokyo 108, Japan). As supplied from Mitutoyo Corporation, the thickness meter contains a spring attached to the probe within the meter housing. This spring is removed to provide a free falling probe, which has a downward force of about 27 grams. In addition, the cap over the top of the probe located on the top of the meter housing is also removed to enable attachment of the probe to the suspension spring 5 (available from McMaster-Carr Supply Co., Chicago, Ill., Item No.9640K41), which serves to counter or reduce the downward force of the probe to about 1 gram, ±0.5 gram. A wire hook can be glued to the top of the probe for attachment to the suspension spring. The bottom tip of the probe is also provided with an extension needle (Mitutoyo Corporation, Part No. 131279) to enable the probe to be inserted into the sample cup.

To carry out the test, a 0.160 gram sample of the superabsorbent material, which has been sieved to a particle size between 300 and 600 microns, is placed into the sample cup. The sample is then covered with a plastic spacer disc, weighing 4.4 grams, which is slightly smaller than the inside diameter of the sample cup and serves to protect the sample from being disturbed during the test. The 100 grams weight is then placed on top of the spacer disc, thereby applying a load of 0.3 pounds per square inch. The sample cup is placed in the Petri dish on the platform of the laboratory jack raised up until it contacts the tip of the probe. The meter is zeroed. A sufficient amount of saline solution is added to the Petri dish (50-100 milliliters) to begin the test. The distance the weight is raised by the expanding sample as it absorbs the saline solution is measured by the probe. This distance, multiplied by the cross-sectional area inside the sample cup, is a measure of the expansion volume of the sample due to absorption. Factoring in the density of the saline solution and the weight of the sample, the amount of saline solution absorbed is readily calculated. The weight of saline solution absorbed after 2, 4, 10 or 30 minutes is the AUL value for that length of time, expressed as grams saline solution absorbed per gram of superabsorbent. If desired, the readings of the modified thickness meter can be continuously input to a computer (Mitutoyo Digimatic Miniprocessor DP-2 DX) to make the calculations and provide AUL readings. As a cross-check, the AUL can also be determined by determining the weight difference between the sample cup before and after the test, the weight difference being the amount of solution absorbed by the sample.

EXAMPLES

In order to illustrate the method of this invention, several superabsorbent materials were subjected to different time/temperature treatments. Specifically, a 10 gram once-dried sample of the superabsorbent material as received from the superabsorbent manufacturer, which had been sieved to a particle size in the range of from 300 to 600 microns, was placed in a glass beaker and thereafter placed in a preheated forced air oven (B-2730-Q, Blue M, Blue Island, Ill.) for a fixed length of time. The sample was removed from the oven and allowed to cool to ambient temperature. The AUL of the sample, at 0.3 pounds per square inch pressure, was then measured at 2 minutes, 4 minutes, 10 minutes and 30 minutes.

The particular superabsorbents tested were: IM-5000P (Starch grafted sodium polyacrylate, Hoechst Celanese Corporation, Portsmouth, Va.); DRYTECH 534 (Partial sodium salt of crosslinked poly(acrylic acid), Dow Chemical Company, Midland, Mich.); FAVOR SAB 835 (Polyacrylate/polyalcohol, Stockhausen, Inc., Greensboro, N.C.); 88-103 (Partial sodium salt of crosslinked poly(acrylic acid), Dow Chemical Company); 88-111 (Partial sodium salt of crosslinked poly(acrylic acid), Dow Chemical Company); KI Gel (isobutylene/maleic anhydride copolymer, Kuraray Co., Ltd., Tokyo, Japan; FOXORB HR (carboxymethylated starch, Avebe, Foxhol, Netherlands); AQUALON (crosslinked carboxymethylated cellulose, (Aqualon Company, Wilmington, Del.).

The results are tabulated in TABLES 1 and 2, in which the effects of treatment time and temperature, respectively, are illustrated.

TABLE 1

(Effect of Treatment Time on AUL)

| SAMPLE | 2 min AUL | 4 min AUL | 10 min AUL | 30 min AUL |
|---|---|---|---|---|
| IM-5000P | | | | |
| Untreated | 2.75 | 4.05 | 8.96 | 24.84 |
| 170° C./ 5 min. | 3.92 | 4.86 | 11.17 | 26.20 |
| 170° C./10 min. | 3.78 | 5.80 | 13.14 | 27.27 |
| 170° C./15 min. | 12.44 | 20.23 | 26.08 | 27.32 |
| 170° C./20 min. | 11.43 | 18.65 | 25.19 | 26.61 |
| 170° C./30 min. | 13.32 | 20.64 | 25.11 | 25.80 |
| 170° C./60 min. | 14.27 | 20.35 | 23.35 | 23.60 |
| DRYTECH 534 | | | | |
| Untreated | 4.06 | 6.25 | 11.67 | 21.49 |
| 180° C./15 min. | 5.08 | 10.63 | 19.30 | 23.94 |
| 180° C./20 min. | 6.43 | 12.34 | 20.76 | 24.68 |
| 180° C./25 min. | 6.18 | 12.13 | 20.33 | 24.08 |
| 180° C./30 min. | 6.37 | 12.48 | 20.76 | 24.48 |
| FAVOR SAB 835 | | | | |
| Untreated | 3.88 | 5.15 | 8.77 | 22.42 |
| 190° C./10 min. | 5.46 | 8.76 | 19.80 | 25.08 |
| 190° C./15 min. | 8.03 | 14.99 | 22.72 | 25.61 |
| 190° C./20 min. | 10.36 | 17.64 | 23.84 | 25.80 |
| 190° C./25 min. | 10.48 | 17.89 | 24.34 | 26.29 |
| 190° C./30 min. | 9.68 | 17.07 | 23.85 | 26.12 |

TABLE 2

(Effect of Treatment Temperature on AUL)

| SAMPLE | 2 min AUL | 4 min AUL | 10 min AUL | 30 min AUL |
|---|---|---|---|---|
| IM-5000P | | | | |
| Untreated | 2.75 | 4.05 | 8.96 | 24.84 |
| 100° C./20 min. | 2.62 | 3.75 | 6.95 | 21.90 |
| 140° C./20 min. | 3.15 | 4.73 | 10.62 | 26.36 |
| 150° C./20 min. | 4.60 | 7.26 | 15.66 | 27.44 |
| 160° C./20 min. | 6.90 | 13.46 | 23.84 | 27.37 |
| 170° C./20 min. | 9.27 | 17.69 | 24.87 | 26.42 |
| 180° C./20 min. | 12.33 | 19.81 | 24.13 | 24.84 |
| 190° C./20 min. | 12.37 | 18.92 | 21.97 | 22.32 |
| 200° C./20 min. | 13.06 | 18.54 | 20.58 | 20.73 |
| DRYTECH 534 | | | | |
| Untreated | 4.06 | 6.25 | 11.67 | 21.49 |
| 170° C./20 min. | 5.78 | 10.71 | 19.47 | 23.97 |
| 180° C./20 min. | 6.43 | 12.34 | 20.76 | 24.68 |
| 190° C./20 min. | 5.09 | 10.95 | 19.39 | 23.32 |
| 200° C./20 min. | 6.47 | 12.78 | 20.61 | 23.69 |
| FAVOR SAB 835 | | | | |
| Untreated | 3.88 | 5.15 | 8.77 | 22.42 |
| 170° C./20 min. | 4.44 | 5.91 | 11.78 | 25.19 |
| 180° C./20 min. | 7.14 | 12.97 | 22.64 | 25.98 |
| 190° C./20 min. | 10.36 | 17.64 | 23.84 | 25.80 |
| 200° C./20 min. | 9.60 | 16.69 | 23.53 | 25.91 |
| 88-103 | | | | |
| Untreated | 9.67 | 16.09 | 22.47 | 24.51 |
| 180° C./20 min. | 9.84 | 16.77 | 22.85 | 24.52 |
| 190° C./20 min. | 12.31 | 19.31 | 24.41 | 25.80 |
| 200° C./20 min. | 13.12 | 20.61 | 24.24 | 24.85 |
| 210° C./20 min. | 13.91 | 20.76 | 22.97 | 23.17 |
| 88-111 | | | | |
| Untreated | 13.61 | 20.96 | 25.50 | 26.53 |
| 180° C./20 min. | 15.34 | 20.94 | 24.21 | 24.92 |
| 190° C./20 min. | 17.15 | 21.84 | 24.23 | 24.75 |
| 200° C./20 min. | 19.00 | 22.41 | 23.82 | 23.99 |
| 210° C./20 min. | 19.26 | 21.75 | 22.36 | 22.43 |
| KI Gel | | | | |
| Untreated | 2.43 | 3.45 | 5.19 | 6.91 |
| 180° C./20 min. | 3.46 | 4.74 | 6.84 | 8.80 |
| 200° C./20 min. | 4.35 | 6.00 | 8.31 | 10.25 |
| FOXORB HR | | | | |
| Untreated | 2.62 | 3.28 | 4.17 | 5.26 |
| 110° C./20 min. | 2.50 | 3.28 | 4.44 | 5.86 |
| 170° C./20 min. | 11.21 | 11.26 | 11.30 | 11.35 |
| AQUALON | | | | |
| Untreated | 1.22 | 1.54 | 2.13 | 3.23 |
| 170° C./20 min. | 2.39 | 2.78 | 3.39 | 4.38 |

The results of these tests illustrate the improvement in AUL which is achieved using the heat treatment of this invention. In all cases, the 2 minute AUL was increased after the superabsorbent material was heat treated at temperatures of 140° C. or greater. Similarly, the 2 minute AUL was increased after being treated for 5 minutes or more for all samples tested.

It will be appreciated that the foregoing examples, given for purposes of illustration, are not to be construed as limiting the scope of the following claims of this invention, which include all equivalents thereto.

I claim:

1. A method of treating a once-dried water-insoluble superabsorbent material comprising heating the once-dried water-insoluble superabsorbent material at a temperature of about 125° C. or greater for a time sufficient to increase the two-minute Absorbency Under Load of the superabsorbent material at least about 1 gram per gram.

2. The method of claim 1 wherein the temperature is about 140° C. or greater.

3. The method of claim 1 wherein the temperature is about 150° C. or greater.

4. The method of claim 1 wherein the temperature is about 160° C. or greater.

5. The method of claim 1 wherein the temperature is about 170° C. or greater.

6. The method of claim 1 wherein the temperature is about 180° C. or greater.

7. The method of claim 1 wherein the temperature is about 190° C. or greater.

8. The method of claim 1 wherein the temperature is about 200° C. or greater.

9. The method of claim 1 wherein the temperature is about 210° C. or greater.

10. The method of claim 1 wherein the temperature is from about 150° C. to about 210° C.

11. The method of claim 1 wherein the superabsorbent material is treated for about 5 minutes or less.

12. The method of claim 1 wherein the superabsorbent material is treated for about 10 minutes or less.

13. The method of claim 1 wherein the superabsorbent material is treated for about 20 minutes or less.

14. The method of claim 1 wherein the superabsorbent material is treated for about 25 minutes or less.

15. The method of claim 1 wherein the superabsorbent material is treated for about 30 minutes or less.

16. The method of claim 1 wherein the superabsorbent material is treated for about 60 minutes or less.

17. The method of claim 1 wherein the superabsorbent material is treated at a temperature of from about 140° C. to about 210° C. for from about 5 to about 60 minutes.

18. The method of claim 1 wherein the superabsorbent material is treated at a temperature of from about 170° C. to about 210° C. for about 20 minutes or less.

19. The method of claim 1 wherein the superabsorbent material is treated at a temperature of from about 170° C. to about 190° C. for about 20 minutes.

20. The method of claim 1 wherein the superabsorbent material is an alkali metal salt of poly(acrylic acid).

* * * * *

UNITED STATES PATENT AND TRADEMARK OFFICE
CERTIFICATE OF CORRECTION

PATENT NO. : 5,206,205
DATED : April 27, 1993
INVENTOR(S) : C. L. Tsai

It is certified that error appears in the above-identified patent and that said Letters Patent is hereby corrected as shown below:

At column 3, line 17, after the word "a", add the following: "100 mesh metal screen having 150 micron openings."

Signed and Sealed this

Eighth Day of November, 1994

Attest:

BRUCE LEHMAN

Attesting Officer     Commissioner of Patents and Trademarks